United States Patent
Lapinski et al.

(10) Patent No.: US 9,302,960 B2
(45) Date of Patent: Apr. 5, 2016

(54) PROCESS FOR PRODUCING A FEED STREAM FOR A STEAM CRACKER

(71) Applicant: UOP LLC, Des Plaines, IL (US)

(72) Inventors: Mark P. Lapinski, Aurora, IL (US); Matthew Lippmann, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 224 days.

(21) Appl. No.: 14/267,845

(22) Filed: May 1, 2014

(65) Prior Publication Data
US 2015/0315102 A1   Nov. 5, 2015

(51) Int. Cl.
| | | |
|---|---|---|
| *C07C 5/27* | (2006.01) | |
| *C07C 6/08* | (2006.01) | |
| *C07C 4/04* | (2006.01) | |
| *C07C 7/00* | (2006.01) | |

(52) U.S. Cl.
CPC . *C07C 7/005* (2013.01); *C07C 4/04* (2013.01); *C07C 5/27* (2013.01)

(58) Field of Classification Search
CPC ............... C07C 5/27; C07C 6/08; C07C 4/04
USPC .................. 585/310, 737, 738, 748, 708, 752
See application file for complete search history.

(56) References Cited

U.S. PATENT DOCUMENTS

| | | | |
|---|---|---|---|
| 3,136,825 A | | 6/1964 | Ryan et al. |
| 3,617,516 A | * | 11/1971 | Van Gooswilligen ... B01J 27/06 208/134 |
| 3,812,199 A | | 5/1974 | Chen et al. |
| 3,953,537 A | | 4/1976 | Chloupek et al. |
| 4,191,845 A | | 3/1980 | Rubin et al. |

(Continued)

FOREIGN PATENT DOCUMENTS

NL    8800685 A    10/1989

OTHER PUBLICATIONS

Rezgui et al., "Pentane isomerization and disproportionation catalyzed by sulfated zirconia promoted with iron and manganese," Catalysis Letters (1996), v. 37(1-2), pp. 5-8.

(Continued)

*Primary Examiner* — Thuan D Dang

(57) ABSTRACT

A process for producing a feed for a stream cracker. At least a portion of the $C_6$ cyclic hydrocarbons are removed from a stream prior to it being passed into an isomerization zone. Disproportionation reaction selectivity is increased, producing valuable $C_3$ hydrocarbons and $C_4$ hydrocarbons. Also, a higher ring opening conversion of $C_5$ cyclic hydrocarbons is observed. The yield may be adjusted by controlling an amount of $C_6$ cyclic hydrocarbons passed to the isomerization zone. The catalyst in the isomerization zone is free of chloride, and the streams including effluent from the isomerization zone may be passed to a steam cracker without requiring chloride removal.

12 Claims, 3 Drawing Sheets

(56) References Cited

U.S. PATENT DOCUMENTS

| | | |
|---|---|---|
| 5,026,951 A | 6/1991 | Schmidt et al. |
| 5,396,016 A | 3/1995 | Jablonski et al. |
| 5,489,727 A | 2/1996 | Randolph et al. |
| 6,423,880 B1 | 7/2002 | Randolph et al. |
| 7,053,261 B2 | 5/2006 | Herbst et al. |
| 7,067,448 B1 | 6/2006 | Weitkamp et al. |
| 7,485,768 B1 | 2/2009 | Rice et al. |
| 7,902,418 B2 | 3/2011 | Schmidt et al. |
| 2005/0101814 A1 | 5/2005 | Foley et al. |
| 2012/0074039 A1 | 3/2012 | Gonzalez et al. |
| 2012/0184794 A1 | 7/2012 | Shecterle |

OTHER PUBLICATIONS

Maness, Jr. et al. "Paraffin isomerization and disproportionation catalyzed by Pd-loaded fluorided mordenites," Journal of Catalysis (1989), v. 117(2), pp. 322-334.

Juszczyk et al., "Neopentane conversion over Pd/$\gamma$-Al2O3," Catalysis Letters (1995), v. 31(1), pp. 37-45.

Karpinski et al., "Reaction of Neopentane with Hydrogen over Pd, Pt, Ir and Rh," Journal of the Chemical Society, Faraday Transactions (1987), v. 83(4), pp. 1293-1305.

* cited by examiner

PROCESS FOR PRODUCING A FEED STREAM FOR A STEAM CRACKER

FIELD OF THE INVENTION

This invention relates to processes for separating out various fractions of a naphtha stream to convert iso-paraffins into normal paraffin in an isomerization zone for producing a feed stream for a steam cracker.

BACKGROUND OF THE INVENTION

Ethylene and propylene are important chemicals for use in the production of other useful materials, such as polyethylene and polypropylene. Polyethylene and polypropylene are two of the most common plastics found in use today and have a wide variety of uses for, for example, a material for fabrication and as a material for packaging. Other uses for ethylene and propylene include the production of vinyl chloride, ethylene oxide, ethylbenzene and alcohol.

The great bulk of the ethylene consumed in the production of the plastics and petrochemicals such as polyethylene is produced by the thermal cracking of higher molecular weight hydrocarbons. Steam is usually mixed with the feed stream to the cracking reactor to reduce the hydrocarbon partial pressure and enhance olefin yield and to reduce the formation and deposition of carbonaceous material in the cracking reactors. The process is therefore often referred to a steam cracking or pyrolysis.

The composition of the feed to the steam cracking reactor affects the results. A fundamental basis of this is the propensity of some hydrocarbons to crack more easily than others. The normal ranking of tendency of the hydrocarbons to crack to ethylene is normally given as: normal paraffins; iso-paraffins; olefins; naphthenes; and, aromatics. Benzene and other aromatics are particularly resistant to steam cracking and undesirable as cracking feed stocks, with only the alkyl side chains being cracked to produce the desired product.

The feed stream to a steam cracking unit can be quite diverse and can be chosen from a variety of petroleum fractions. The feed stream to the subject process preferably has a boiling point range falling within the naphtha boiling point range or about 36° C. to 205° C. It is preferred that the feed stream does not contain appreciable amounts, e.g. more than 5 mole %, of $C_{12}$ hydrocarbons. A representative feed stream to the subject process is a $C_5$-$C_{11}$ fraction produced by fractional distillation of a hydrotreated petroleum fraction. Hydrotreating is desired to reduce the sulfur and nitrogen content of the feed down to acceptable levels. A second representative feed is a similar fraction comprising $C_5$ through $C_9$ hydrocarbons.

The feed to a steam cracking unit is also normally a mixture of hydrocarbons varying both by type of hydrocarbon and carbon number. This variety results in it being very difficult to separate less desirable feed components, such as naphthenes and aromatics, from the feed stream by fractional distillation. The hydrocarbons that are not the normal paraffins can be removed by solvent extraction or adsorption. These hydrocarbons can be upgraded to improve the feedstock to the steam cracking unit.

One way to upgrade these hydrocarbons is to pass the non-normal paraffins to an isomerization zone. In the isomerization zone, the non-normal paraffins are converted, in the presence of a catalyst, into normal paraffins.

Many isomerization zones utilize a catalyst which contains, among other things, chloride. It is common for the catalyst to lose small amounts of the chloride into the effluent from the isomerization zones. Steam crackers, however, are very sensitive to the presence of chloride in the product stream. Accordingly, any product streams from isomerization zones which have a chlorided-catalyst must be further treated in order to minimize most, if not all, of the chloride from the product stream as it is passed into the steam cracker. One such method involves an adsorption zone which can remove most of the chloride from the effluent streams from the isomerization zone.

It would be desirable to have a process which produces a feed stream for a steam cracker which does not require a treatment to remove chloride prior to passing to the steam cracker.

SUMMARY OF THE INVENTION

It has been discovered that conversion to normal paraffins in the isomerization zone can be increased by removing, or at least reducing, the amount of $C_6$ cyclic hydrocarbons in the stream passing into the isomerization zone occurs with a variety of isomerization catalysts, including non-chlorided catalysts.

Accordingly, in a first embodiment of the invention a process for increasing a yield of an isomerization zone is provided by: separating a portion of $C_6$ cyclic hydrocarbons from a naphtha stream comprising $C_5$+ hydrocarbons to provide a $C_6$ cyclic hydrocarbons lean stream; separating i$C_5$ hydrocarbons and i$C_6$ hydrocarbons from the $C_6$ cyclic hydrocarbons lean stream; and, passing at least one stream being rich in i$C_5$ hydrocarbons, i$C_6$ hydrocarbons, or both to an isomerization zone. The isomerization zone includes only non-chloride containing catalyst.

In some embodiments, the process further includes controlling an amount of $C_6$ cyclic hydrocarbons passed into the isomerization zone. The amount of $C_6$ cyclic hydrocarbons passed into the isomerization zone may be controlled by selectively adding a stream of $C_6$ cyclic hydrocarbons to the isomerization zone, by controlling an operating parameter of a separation zone used to separate the $C_6$ cyclic hydrocarbons from the naphtha stream, or by a combination thereof.

In at least one embodiment, the process further includes passing at least one stream comprising a portion of an effluent from the isomerization zone to a steam cracker. The at least one stream may be passed from the isomerization zone to a stream cracker without being treated to remove chloride.

It is contemplated that the process includes separating an effluent from the isomerization zone into an overhead stream comprising $C_4$- hydrocarbons and a bottoms stream comprising $C_5$+ hydrocarbons and passing at least one stream from the isomerization zone to a steam cracker.

In some embodiments, the process may include passing the naphtha stream to a first separation zone and separating the naphtha stream in the first separation zone into an overhead stream and a bottoms stream. The overhead stream may be the $C_6$ cyclic hydrocarbons lean stream and the bottoms stream may be rich in n-hexane and $C_6$ cyclic hydrocarbons. The overhead stream may be passed from the first separation zone to a second separation zone and separated into the at least one stream being rich in i$C_5$ hydrocarbons, i$C_6$ hydrocarbons, or both.

It is contemplated that the overhead stream from the first separation zone is separated in a first separator column of the second separation zone into an overhead stream, an intermediate stream, a bottoms stream. The overhead stream from the first separator column of the second separation zone may be rich in $C_5$ hydrocarbons and the intermediate stream of the first separator column of the second separation zone may be rich in $iC_6$ hydrocarbons. It is further contemplated that the overhead stream from the first separator column of the second separation zone is separated in a second separator column of the second separation zone into an overhead stream and a bottoms stream. The overhead stream of the second separator column of the second separation zone may be rich in $iC_5$ hydrocarbons. The bottoms stream from the isomerization zone may be recycled to the first column from the second separation zone. The bottoms stream from the first separator column and the second separator column may be combined and may also be passed to a steam cracker.

In some embodiments of the present invention, the second separation zone comprises at least one adsorption zone. The process may further include separating the overheads stream from the first separation zone in the at least one absorption zone into a first stream and a second stream. The first stream may be rich in $iC_5$ hydrocarbons and $iC_6$ hydrocarbons and the second stream may be rich in n-pentane and n-hexane. The bottoms stream from the isomerization zone may be recycled back to the first separation zone or the second separation zone, or both.

In yet another embodiment of the present invention, a process for increasing a yield of an isomerization zone is provided which includes: removing $C_6$ cyclic hydrocarbons from at least one stream comprising $iC_5$ hydrocarbons, $iC_6$ hydrocarbons, or both, to provide a $C_6$ cyclic hydrocarbons lean stream; passing the $C_6$ cyclic hydrocarbons lean stream an isomerization zone; separating an effluent from the isomerization zone into an overhead stream comprising $C_4$– hydrocarbons and a bottoms stream comprising $C_5$+ hydrocarbons; and, passing at least one stream from the isomerization zone to a steam cracker. The isomerization zone includes catalyst comprising only non-chloride containing catalyst.

It is contemplated that at least one stream from the isomerization zone may be passed to the first separation zone so that a portion of the at least one stream from the isomerization zone is capable of passing to the steam cracker. The $C_6$ cyclic hydrocarbons may be separated in a first separation zone, and n-pentane and n-hexane are separated from the $C_6$ cyclic hydrocarbons lean stream in a second separation zone.

It is further contemplated that at least one stream from the isomerization zone may be passed to the second separation zone so that a portion of the at least one stream from the isomerization zone is capable of passing to the steam cracker.

Additional embodiments and details of the present invention are set forth in the following detailed description of the invention.

DETAILED DESCRIPTION OF THE DRAWINGS

The drawings are simplified process diagrams in which.

DETAILED DESCRIPTION OF THE INVENTION

As mentioned above, it has been discovered that the conversion to normal paraffins in the isomerization zone can be increased by removing a portion of the $C_6$ cyclic hydrocarbons, such as cyclohexane, methyl-cyclopentane, and benzene, in the stream passing into the isomerization zone. Specifically, when the amount of $C_6$ cyclic hydrocarbons in the stream has been reduced, disproportionation reactions occur which lead to increased amounts of valuable $C_3$ hydrocarbons and $C_4$ hydrocarbons, as well as increases in the per pass conversion of the iso-paraffin hydrocarbons in the feed. The products from the disproportionation reactions undergo isomerization reactions leading to an increase in yields of normal paraffins according to the various embodiments of the present invention.

Concomitantly, the increase in yield has been observed over various catalysts, including those without chloride. Thus, not only does this allow for an increase in the amount of normal paraffins, the process also eliminates the needed to remove chloride from the product stream prior to passing to a steam cracker. Thus, a process is provided which has an increased normal paraffins yield and which does not have to be further treated to remove chloride prior to passing to a steam cracker. As will be appreciated, this will lower both the capital expenditures and the operating expenses associated with the operation of the steam cracking units.

Figure 1:
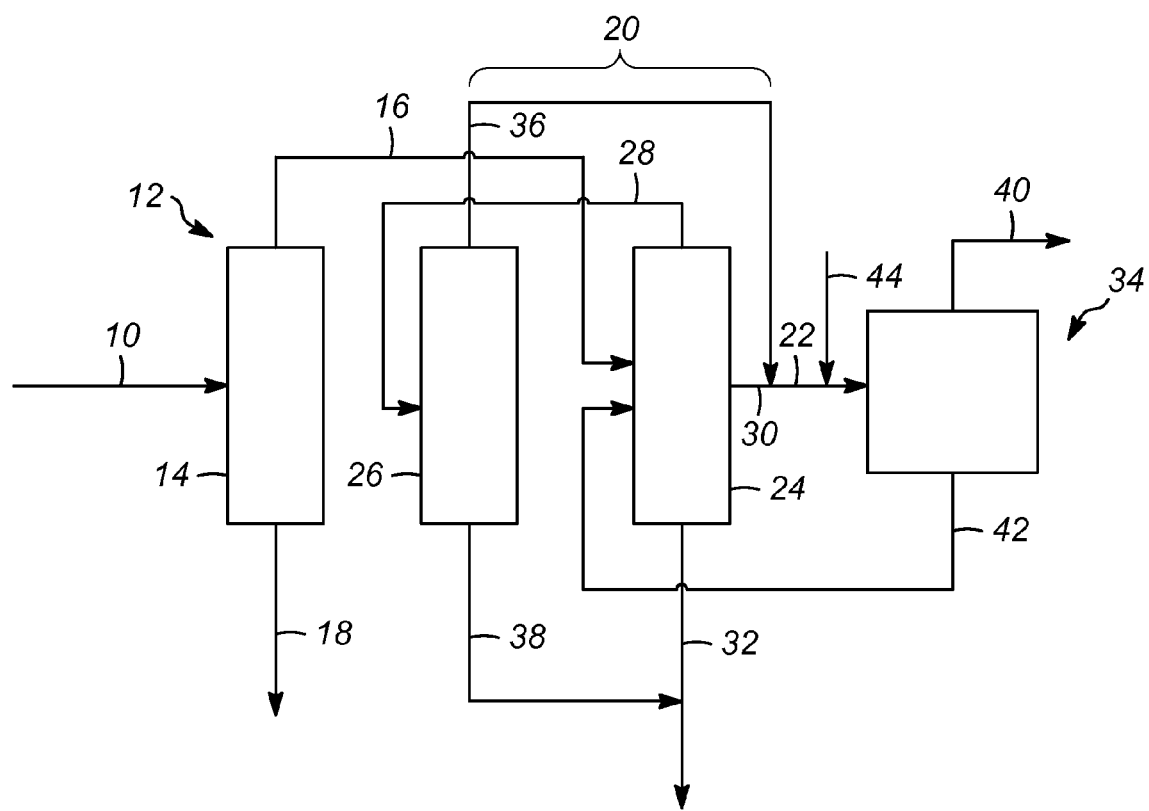
FIG. 1 shows a process flow diagram of a process according to one embodiment of the present invention.

A first embodiment of the present invention is shown in FIG. 1, in which a feed stream 10 is passed into a first separation zone 12. The feed stream 10 is preferably hydrotreated naphtha comprising $C_5$+ hydrocarbons (meaning hydrocarbons having five or more carbon atoms).

The first separation zone 12 may include a separator column 14, such as a fractionation column. As will be appreciated, the depiction of column 14 is simplified as all the auxiliary operational components, such as controls, trays, condenser and reboiler, may be of conventional design. In other embodiments, the feed stream 10, or multiple feed streams, can be fed into the column 14 at different locations if appropriate. The column 14 will typically contain conventional vapor-liquid contacting equipment such as trays or packing. The type of tray and design details such as tray type, tray spacing and layout may vary within the column 14.

The column 14 will separate the feed stream 10 into an overhead stream 16 and a bottoms stream 18. The overhead stream 16 may comprise $C_5$ hydrocarbons and $iC_6$ hydrocarbons. Since at least a portion of the $C_6$ cyclic hydrocarbons have been removed from the portion of the feed stream 10 in the overhead stream 16, the overhead stream 16 will be a $C_6$ cyclic hydrocarbons lean stream. The bottoms stream 18 may comprise n-hexane, $C_6$ cyclic hydrocarbons, and $C_7$+ hydrocarbons. Furthermore, depending on the operating conditions of the column 14, the bottoms stream 18 may also contain some small amounts of $iC_6$ hydrocarbons, such as 3-methylpentane. The bottoms stream 18 may be passed to various other zones, such as, for example: to saturation and then to a steam cracker; to a reformer and then to an aromatic complex; to saturation, then to a ring operating reactor, and then to a steam cracker; or a combination of the foregoing. The further processing of the bottoms stream 18 is not necessary for the understanding and practicing of the present invention.

Returning to FIG. 1, the overhead stream 16 from the first separation zone 12 may be passed to a second separation zone 20. The second separation zone 20 provides at least one stream 22 that is rich in $iC_5$ hydrocarbons, $iC_6$ hydrocarbons, or both. In a preferred embodiment, the second separation zone 20 comprises at least two columns 24, 26. These two columns 24, 26 may also be fractionation columns.

The first column 24 in the second separation zone 20 may receive the overhead stream 16 from the first separation zone 12. In this embodiment of the present invention, the first column 24 separates the overhead stream 16 into three streams, and thus may comprise a divided wall column. Such divided wall columns are known, for example, from U.S. Pat. No. 6,927,314, the entirety of which is incorporated herein by reference. The three streams produced by the first column 24 are an overhead stream 28, an intermediate stream 30, and a bottoms stream 32.

The overhead stream 28 from the first column 24 in the second separation 20 zone comprises $C_5$ hydrocarbons. The intermediate stream 30 comprises $iC_6$ hydrocarbons. The bottoms stream 32 comprises $C_6$ cyclic hydrocarbons, $C_7+$ hydrocarbons and n-hexane which either were not separated out in the first separation zone 12 or which were formed in the isomerization zone.

The bottoms stream 32 from the first column 24 in the second separation zone 20 may be passed to various other zones, such as, for example a steam cracker. Again, the further processing of the bottoms stream 32 is not necessary for the understanding and practicing of the present invention.

The intermediate stream 30 has a high concentration of $iC_6$ hydrocarbons, compared to the concentration of $iC_6$ hydrocarbons in the feed stream 10. Thus, the intermediate stream 30 is considered an $iC_6$ hydrocarbon rich stream. The intermediate stream 30 may be passed to an isomerization zone 34, discussed in more detail below.

The overhead stream 28 from the first column 24 is passed to the second column 26 in the second separation zone 20. In the second column 26, the overhead stream 28 from the first column 24 of the second separation zone 20 is separated into an overhead stream 36 and a bottoms stream 38. The bottoms stream 38 comprises n-pentane and may be combined with bottoms stream 32 from the first column 24 in the second separation zone 20 and passed to, for example, a steam cracker. The further processing of this stream 38 is not necessary for the understanding and practicing of the present invention.

The overhead stream 36 from the second column 26 in the second separation zone 20 comprises $iC_5$ hydrocarbons. Again, since the concentration of $iC_5$ hydrocarbons in this stream 36 is higher than the concentration of $iC_5$ hydrocarbons in the feed stream 10, it is an $iC_5$ hydrocarbon rich stream. The overhead stream 36 from the second column 26 of the second separation zone 20 may be passed to the isomerization zone 34, discussed below. It may be combined with the intermediate stream 30 from the first column 24 of the second separation zone 20. Since both the $iC_5$ hydrocarbons and the $iC_6$ hydrocarbons streams 36, 30 were separated from a portion of the $C_6$ cyclic hydrocarbons lean stream, the amount of $C_6$ cyclic hydrocarbons passed to the isomerization zone 34 is lower.

In the isomerization zone 34, the $iC_5$ hydrocarbons and the $iC_6$ hydrocarbons, in the presence of hydrogen and a catalyst, are converted into normal paraffins. The isomerization zone 34, as is known, typically contains a series of reactors and a separation column. It is preferred that both the $iC_5$ hydrocarbons and the $iC_6$ hydrocarbons streams 36, 30 are passed to the same isomerization zone 34; however it is contemplated that two separate isomerization zones can be used.

While it is known that cracking of some of the paraffins can occur in an isomerization zone 34 to form $C_4-$ hydrocarbons, the conversion of $iC_5$ and $iC_6$ hydrocarbons increases significantly via disproportionation reactions due to the fact that the stream(s) 36, 30 passed into the isomerization zone 34 are lean in $C_6$ cyclic hydrocarbons. It is believed that the disproportionation reactions occur by the combination of two iso-paraffin hydrocarbons followed by scission into one lighter hydrocarbon and one heavier hydrocarbon. For example, two $iC_5$ hydrocarbons can combine and form an $iC_4$ hydrocarbon and an $iC_6$ hydrocarbon in the presence of hydrogen. The $iC_4$ hydrocarbons can further react via disproportionation to form a $C_3$ hydrocarbon and an $iC_5$ hydrocarbon. A significant portion of the produced $iC_4$ hydrocarbons also converts to $nC_4$ hydrocarbons via isomerization reactions in the isomerization zone. A surprising result of the present invention is the production of $C_3$ and $C_4$ normal paraffins via disproportionation and isomerization reactions with low production of low-value undesired methane as a cracked product. Thus, there is an increase in the overall yield of the normal paraffins.

This surprising result is enabled by the use of an isomerization catalyst such as chlorided alumina, sulfated zirconia, tungstated zirconia or zeolite-containing isomerization catalysts. The isomerization catalyst may be amorphous, e.g. based upon amorphous alumina, or zeolitic. A zeolitic catalyst would still normally contain an amorphous binder. The catalyst may comprise a sulfated zirconia and platinum as described in U.S. Pat. No. 5,036,035 and European patent application 0 666 109 A1 or a platinum group metal on chlorided alumina as described in U.S. Pat. No. 5,705,730 and U.S. Pat. No. 6,214,764. Another suitable catalyst is described in U.S. Pat. No. 5,922,639. U.S. Pat. No. 6,818,589 discloses a catalyst comprising a tungstated support of an oxide or hydroxide of a Group IVB (IUPAC 4) metal, preferably zirconium oxide or hydroxide, at least a first component which is a lanthanide element and/or yttrium component, and at least a second component being a platinum-group metal component. These documents are incorporated herein for their teaching as to catalyst compositions, isomerization operating conditions and techniques.

While it is contemplated that any appropriate isomerization catalyst could be used, for the production of a feed stream it is contemplated and preferred that the catalyst is a non-chlorided catalyst, such as a sulfated zirconia catalyst. As mentioned above, since such a catalyst does not contain chloride, there is no need to further treat the streams containing effluent from the isomerization zone 34.

Contacting within the isomerization zone 34 may be effected using the catalyst in a fixed-bed system, a moving-bed system, a fluidized-bed system, or in a batch-type operation. The reactants may be contacted with the bed of catalyst particles in upward, downward, or radial-flow fashion. The reactants may be in the liquid phase, a mixed liquid-vapor phase, or a vapor phase when contacted with the catalyst particles, with a mixed phase or vapor phase being preferred. The isomerization zone may be in a single reactor or in two or more separate reactors with suitable means therebetween to insure that the desired isomerization temperature is maintained at the entrance to each zone. Two or more reactors in sequence enable improved isomerization through control of individual reactor temperatures and for partial catalyst replacement without a process shutdown.

Returning to FIG. 1, a first stream 40 recovered from the isomerization zone comprises $C_4-$ hydrocarbons. This stream 40 may be sent to gas treatment, then to a steam cracker, or it may be sent to gas treatment, separation, and an $iC_4$ hydrocarbons stream may be sent to another isomerization zone. The further processing of this stream 40 is not necessary for the understanding and practicing of the present invention except in that this stream would need to be treated to remove chloride before being sent to a steam cracker if a chlorided alumina catalyst was used in the isomerization zone.

A second stream 42 recovered from the isomerization zone 34 will comprise $C_5+$ hydrocarbons, including normal paraffins. This stream 42 may be sent back through the first and second separation zones 12, 20 to separate out the normal paraffins from the iso-paraffins. In a most preferred embodiment, this stream 42 is passed back to the first column 24 of the second separation zone 20. The normal hydrocarbons in this stream will be separated out with the $C_6$ cyclic hydrocarbons lean stream 16 passing through the second separation zone 20 and can be further processed as mentioned above.

Figure 2:
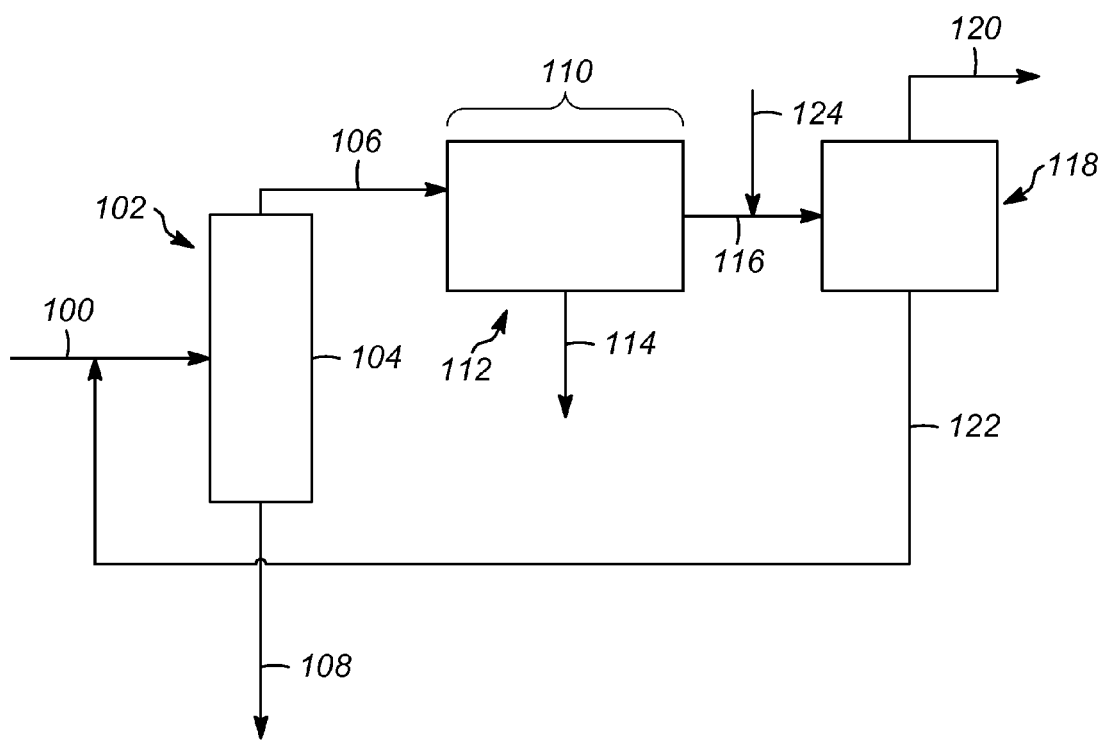
FIG. 2 shows a process flow diagram of a process according to another embodiment of the present invention; and, FIG. 3 shows a process flow diagram of a process according to another embodiment of the present invention.

Turning to FIG. 2, another embodiment of the present invention is shown. In this embodiment, a feed stream 100 is also passed into a first separation zone 102. The feed stream 100 is preferably hydrotreated naphtha comprising $C_5+$ hydrocarbons.

The first separation zone 102 may include a separator column 104, such as a fractionation column. This column 104 preferably functions identically to the column 14 in the embodiment shown in FIG. 1. Thus, the feed stream 100 will separate into an overhead stream 106 and a bottom stream 108. However, it is also contemplated that the first separation zone 102 comprises an adsorption zone (discussed below).

The overhead stream 106 may comprise $C_5$ hydrocarbons and $iC_6$ hydrocarbons identical to stream 16 in the embodiment in FIG. 1. Since the $C_6$ cyclic hydrocarbons have been removed from the portion of the feed stream 100 in the overhead stream 106, the overhead stream 106 will be a $C_6$ cyclic hydrocarbons lean stream. The bottom stream 108 may comprise n-hexane, $C_6$ cyclic hydrocarbons, and $C_7+$ hydrocarbons and a small amount of iC6 hydrocarbons. The bottoms stream 108 may be passed to various other zones, such as, for example: to saturation and then to a steam cracker; to a reformer and then to an aromatic complex; to saturation, then to a ring operating reactor, and then to a steam cracker; or a combination of the foregoing. The further processing of bottoms stream 108 is not necessary for the understanding and practicing of the present invention.

Returning to FIG. 2, the overhead stream 106 from the first separation zone 102, may be passed to a second separation zone 110. In this embodiment of the present invention, it is contemplated that the second separation zone 110 comprises an adsorption zone 112.

The adsorption zone 112 can include, as is known, a single large bed of adsorbent or in several parallel beds on a swing bed basis. However, it has been found that simulated moving bed adsorptive separation provides several advantages such as high purity and recovery. Therefore, many commercial scale petrochemical separations especially for the recovery of mixed paraffins are performed using simulated countercurrent moving bed (SMB) technology. Further details on equipment and techniques for operating an SMB process may be found in U.S. Pat. Nos. 3,208,833; 3,214,247; 3,392,113; 3,455,815; 3,523,762; 3,617,504; 4,006,197; 4,133,842; and 4,434,051, all of which are incorporated by reference in their entirety. A different type of simulated moving bed operation which can be performed using similar equipment, adsorbent and conditions but which simulates co-current flow of the adsorbent and liquid in the adsorption chambers is described in U.S. Pat. Nos. 4,402,832 and 4,498,991, which are incorporated by reference in their entirety.

Operating conditions for the adsorption chamber used in the subject invention include, in general, a temperature range of from about 20° C. to about 250° C. Adsorption conditions also preferably include a pressure sufficient to maintain the process fluids in liquid phase; which may be from about atmospheric to about 600 psig. Desorption conditions generally include the same temperatures and pressure as used for adsorption conditions. It is generally preferred that an SMB process is operated with an A:F flow rate through the adsorption zone in the broad range of about 1:1 to 5:0.5 where A is the volume rate of "circulation" of selective pore volume and F is the feed flow rate. The practice of the subject invention requires no significant variation in operating conditions or desorbent composition within the adsorbent chambers. That is, the adsorbent preferably remains at the same temperature throughout the process during both adsorption and desorption.

The adsorbent used in the first adsorption zone preferably comprises aluminosilicate molecular sieves having relatively uniform pore diameters of about 5 angstroms. This is provided by commercially available type 5A molecular sieves produced by UOP LLC.

A second adsorbent which could be used in the adsorption zone comprises silicalite. Silicalite is well described in the literature. It is disclosed and claimed in U.S. Pat. No. 4,061,724 issued to Grose et al., which is incorporated by reference in its entirety. A more detailed description is found in the article, "Silicalite, A New Hydrophobic Crystalline Silica Molecular Sieve," Nature, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å and 5.1-5.7 Å elliptical on the major axis. This gives silicalite great selectivity as a size selective molecular sieve. Due to its aluminum free structure composed of silicon dioxide, silicalite does not show ion-exchange behavior. Silicalite is also described in U.S. Pat. Nos. 5,262,144; 5,276,246 and 5,292,900, which are incorporated by reference in their entirety. These basically relate to treatments which reduce the catalytic activity of silicalite to allow its use as an adsorbent.

The active component of the adsorbent is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders.

The active molecular sieve component of the adsorbent will preferably be in the form of small crystals present in the adsorbent particles in amounts ranging from about 75 to about 98 wt % of the particle based on volatile-free composition. Volatile-free compositions are generally determined at 900° C., after the adsorbent has been calcined, in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt %.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

U.S. Pat. No. 4,992,618 issued to S. Kulprathipanja, and which is incorporated by reference in its entirety, describes the use of a "prepulse" of a desorbent component in an SMB process for recovering normal paraffins. The prepulse is intended to improve the recovery of the extract normal paraffins across the carbon number range of the feed. The prepulse enters the adsorbent chamber at a point before (downstream) the feed injection point. A related SMB processing technique is the use of "zone flush." The zone flush forms a buffer zone between the feed and extract bed lines to keep the desorbent from entering the adsorption zone. While the use of a zone flush requires a more complicated, and thus more costly rotary valve, the use of zone flush is preferred in the adsorption zones when high purity extract product are desired. In practice, a quantity of the mixed component desorbent recovered overhead from the extract and raffinate columns may be passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference in their entirety for their teaching on these aspects of SMB technology.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, the raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

In an SMB process the several steps e.g. adsorption and desorption, are being performed simultaneously in different parts of the mass of adsorbent retained in the adsorbent chamber(s) of the process. If the process was being performed with two or more adsorbent beds in a swing bed system then the steps may be performed in a somewhat interrupted basis, but adsorption and desorption will most likely occur at the same time.

Returning to FIG. 2, a first stream 114 and a second stream 116 are recovered from the adsorption zone 112. The first stream 114 comprises normal paraffins. The first stream 114, being rich in normal paraffins, may be sent to, for example, a stream cracker.

The second stream 116 recovered from the adsorption zone 112 comprises iso-paraffins, or is rich in $iC_5$ and $iC_6$ hydrocarbons. This stream 116 is passed to an isomerization zone 118. As with the isomerization zone 34 in the embodiment shown in FIG. 1, in the isomerization zone 118 of this embodiment, the $iC_5$ and $iC_6$ hydrocarbons, in the presence of hydrogen and an isomerization catalyst, are converted into normal paraffins.

As the stream 116 introduced into the isomerization zone 118 is lean in $C_6$ cyclic hydrocarbons, there is a surprising and unexpected increase in the conversion yields to desirable normal paraffins believed to be produced via disproportionation and isomerization reactions. The specifics of this isomerization zone 118 are the same as discussed above, and thus, are incorporated herein to the discussion of this embodiment.

At least two streams 120, 122 may also be recovered from the isomerization zone 118. The first stream 120 comprises $C_4$- hydrocarbons. This stream 120 may be sent to gas treatment, then to a steam cracker, or it may be sent to gas treatment, separation, and an $iC_4$ hydrocarbons stream may be sent to another isomerization zone. The further processing of this stream 120 is not necessary for the understanding and practicing of the present invention except in that this stream would need to be treated to remove chloride before being sent to a steam cracker if a chlorided alumina catalyst was used in the isomerization zone.

The second stream 122 recovered from the isomerization zone 118 will again comprise $C_5$+ hydrocarbons, including normal paraffins. This stream 122 may be recycled or passed back to the first separation zone 102, the second separation zones 110, or both to separate out the normal paraffins from the iso-paraffins. For example, the stream 122 is passed back to the first separation zone 102. It may or may not be combined with fresh feed stream 100 entering the first separation zone 102. The normal hexane will be separated out in the first separation zone 102, while the normal pentane will be separated out in the second separation zone 110. The normal paraffins will be passed along to further processing units, as discussed above.

Figure 3:
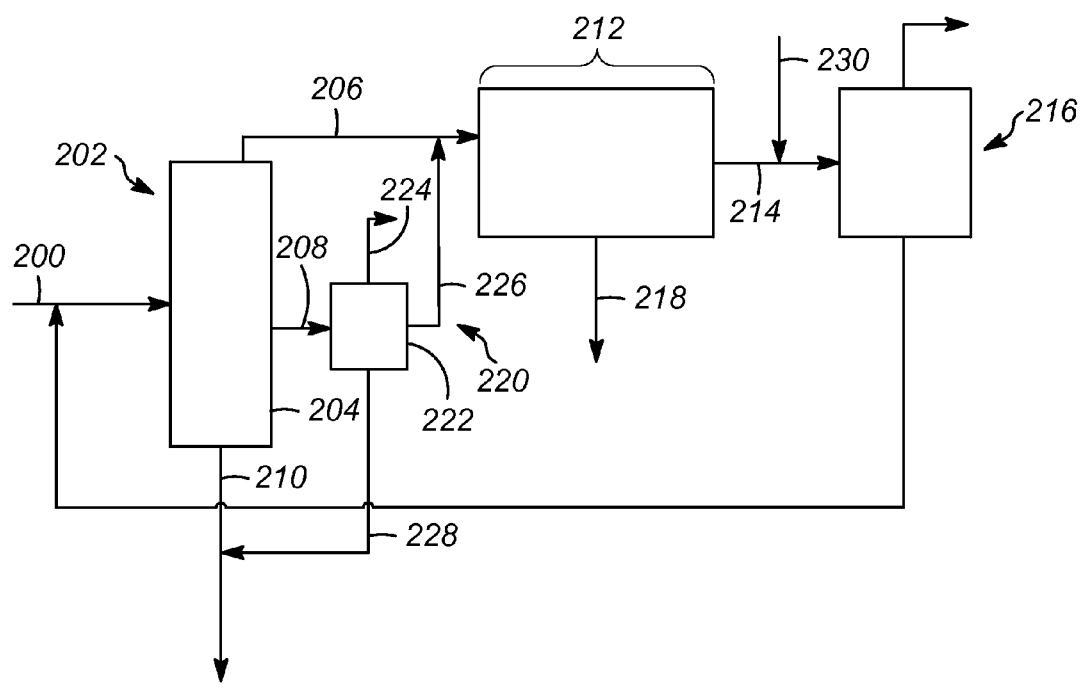

In a third embodiment according to the present invention as shown in FIG. 3, a feed stream 200 is passed into a first separation zone 202. The feed stream 200 is preferably hydrotreated naphtha comprising $C_5+$ hydrocarbons.

The first separation zone 202 may also include a separator column 204, such as a fractionation column. This column 204 will separate the feed stream 200 into an overhead stream 206, an intermediate stream 208, and a bottom stream 210. The overhead stream 206 may once again comprise $C_5$ hydrocarbons and $iC_6$ hydrocarbons. The intermediate stream 208 may comprise n-hexane and $C_6$ cyclic hydrocarbons. The bottoms stream 210 may comprise $C_7+$ hydrocarbons. Since the $C_6$ cyclic hydrocarbons have been removed from the portion of the feed stream 200 in the overhead stream 206, the overhead stream 206 will be a $C_6$ cyclic hydrocarbons lean stream. The bottoms stream 210 may be passed to various other zones, such as, for example: to saturation and then to a steam cracker; to a reformer and then to an aromatic complex; to saturation, then to a ring operating reactor, and then to a steam cracker; or a combination of the foregoing. The further processing of bottoms stream 210 is not necessary for the understanding and practicing of the present invention.

The overhead stream 206 may be passed to a second separation zone 212. It is contemplated that the second separation 212 is either a plurality of separation columns (such as the second separation zone 20 in the embodiment shown in FIG. 1), or an adsorption zone (such as the second separation zone 110 shown in FIG. 2). Accordingly, the portions of those embodiments are incorporated herein.

A first stream 214 from the second separation zone 212, rich in iso-paraffins, is passed to an isomerization zone 216. A second stream 218, rich in normal paraffins, from the second separation zone 212 may be passed to further processing zones. The isomerization zone 216 and the processing of the second stream 218 from the second separation zone may be the same as discussed above with respect to the other embodiments of the present invention.

The difference between this embodiment and the previously discussed embodiments is the intermediate stream 208 from the first separation zone 202. In this embodiment, the intermediate stream 208 from the first separation zone 202 is passed to a ring opening reaction zone 220.

In the ring opening reaction zone 220, the cyclic hydrocarbons, in the presence of a catalyst, are converted into straight chain hydrocarbons. Typically, such reactions occur in a ring opening reactor 222. Such ring opening reactors are known, for example, as disclosed in U.S. Pat. Pub. N. 2005/0101814, incorporated herein by reference. The products of the ring opening reactor 222, which can include methane to $C_7+$ hydrocarbons, may be separated into a $C_4-$ hydrocarbon stream 224, a $C_5$ hydrocarbon and $C_6$ hydrocarbon stream 226, and a $C_6$ cyclic hydrocarbons and $C_7+$ hydrocarbons stream 228. The $C_6$ cyclic hydrocarbons and $C_7+$ hydrocarbons stream 228 may be combined with the bottoms stream 210 from the first separation zone 202. The $C_4-$ hydrocarbon stream 224 may be passed to further processing units or zones. The $C_5$ hydrocarbon and $C_6$ hydrocarbon stream 226 may be combined with the overhead stream 206 of the first separation zone 202, and thus passed to the separation zone 212 and isomerization zone 216.

In any of the above embodiments, the isomerization conditions in the isomerization zones 34, 118, 216 include average reactor temperatures usually ranging from about 40° C. to 250° C. Reactor operating pressures generally range from about 100 kPa to 10 MPa absolute. Liquid hourly space velocities (LHSV) range from about 0.2 to about 25 volumes of isomerizable hydrocarbon feed per hour per volume of catalyst.

Hydrogen is admixed with or remains with the isomerization feed to the isomerization zone to provide a mole ratio of hydrogen to hydrocarbon feed of from about 0.01 to 20. The hydrogen may be supplied totally from outside the process or supplemented by hydrogen recycled to the feed after separation from isomerization reactor effluent. Light hydrocarbons and small amounts of inerts such as nitrogen and argon may be present in the hydrogen. Water should be removed from hydrogen supplied from outside the process, preferably by an adsorption system as is known in the art.

Furthermore, it is contemplated that an amount of $C_6$ cyclic hydrocarbons passed to the isomerization zone is adjusted. This is believed to allow for control of at least the disproportionation reactions and the customization of the product streams. For example, an operating parameter of the various separation zones may be controlled so that an amount of $C_6$ cyclic hydrocarbons does reach the isomerization zone. Additionally, and alternatively, a $C_6$ cyclic hydrocarbons rich stream 44, 124, 230 may be introduced into the steams passing into the isomerization zone.

While the above described embodiments were discussed with respect to $iC_5$ and $iC_6$ hydrocarbons being passed to the isomerization zone for conversion into normal paraffins, it is also contemplated that $iC_4$ hydrocarbons are also contained in the feed streams passed into the isomerization zone for conversion into normal butane. Indeed, this configuration may be desirable as it may reduce the number of isomerization zones or further downstream processing units.

The above described embodiments are merely exemplary, and it is contemplated that other schemes and processes to provide a stream a $C_6$ cyclic lean hydrocarbons to an isomerization zone to produce normal paraffins for a steam cracker feed may be practiced and still fall within the scope of the present invention.

To demonstrate the disproportionation reactions on a chlorided-alumina catalyst that contained platinum, the catalyst was loaded and operated under isomerization conditions of 3.1 MPa (450 psig), with a 0.06 outlet hydrogen to hydrocarbon feed ($H_2$/HC) mole ratio, and at a rate of 2 $h^{-1}$ LHSV with an average temperature of approximately 174.4° C. (346° F.).

Feed A, which comprised 97% $iC_5$ and 3% $nC_5$ hydrocarbons and which contained no $C_6$ cyclic hydrocarbons, was processed. As shown in Table 1 for Product A, significant quantities of $C_6$ and $C_4$ hydrocarbons were made via disproportionation reactions, such as $2iC_5 \rightarrow iC_4 + iC_6$. The normal paraffins that are produced are a result of isomerization reactions such as $iC_4 \leftrightarrows nC_4$ which are limited by equilibrium. The $C_3$ hydrocarbons that are produced are a result of the disproportionation reaction $2iC_4 \rightarrow C_3 + iC_5$.

TABLE 1

| COMPONENTS (wt %) | FEED A | PRODUCT A |
|---|---|---|
| $H_2$ | — | 0.2 |
| $C_1$ | — | 0.1 |
| $C_2$ | — | 0.1 |
| $C_3$ | — | 1.3 |

TABLE 1-continued

| COMPONENTS (wt %) | FEED A | PRODUCT A |
|---|---|---|
| $iC_4$ | 0.0 | 9.6 |
| $nC_4$ | 0.0 | 3.8 |
| $iC_5$ | 96.8 | 53.4 |
| $nC_5$ | 3.1 | 18.0 |
| $iC_6$ | 0.0 | 11.8 |
| $nC_6$ | 0.0 | 1.7 |
| Cyclopentane (CP) | 0.0 | 0.0 |
| Methylcyclopentane (MCP) | 0.0 | 0.0 |
| Cyclohexane (CH) | 0.0 | 0.0 |
| Benzene (BZ) | 0.0 | 0.0 |
| $C_7+$ | 0.0 | 0.2 |
| SUM | 100.0 | 100.0 |
| $iC_5$ converted (%) | — | 44.9 |
| $nC_5 + nC_6$ | 3.1 | 19.8 |
| $C_2, C_3, nC_4, nC_5, nC_6$ | 3.1 | 24.9 |

As can be seen in Table 1, the sum of $C_2$ to $C_6$ normal paraffins was higher at 24.9 wt % when including the products from disproportionation as compared to 19.8 wt % yield when only including the $nC_5$ and $nC_6$ hydrocarbons from isomerization.

In a second experiment, another chlorided-alumina catalyst that contained platinum was loaded and operated under isomerization conditions of 3.1 MPa (450 psig), a 0.2 outlet $H_2$/HC mole ratio and a rate 2 $h^{-1}$ LHSV with an average temperature at about 176.6° C. (350° F.). Feed B was rich in $iC_5$ and $iC_6$ hydrocarbons and contained 1.46% cyclopentane (CP). Feed C was similar to Feed B with 1.42 wt % cyclopentane but also contained 1.29 wt % cyclohexane (a $C_6$ cyclic hydrocarbon). With the $C_6$ cyclic hydrocarbon in Feed C, as shown in Table 2, the amount of $C_3$ and $C_4$ hydrocarbons were greatly reduced (compare Product C vs. Product B). This demonstrates that the presence of the $C_6$ cyclic hydrocarbon significantly decreased the disproportionation reactions.

TABLE 2

| COMPONENTS (wt %) | FEED B | PRODUCT B | FEED C | PRODUCT C |
|---|---|---|---|---|
| $H_2$ | | 0.5 | | 0.5 |
| $C_1$ | | 0.2 | | 0.1 |
| $C_2$ | | 0.3 | | 0.1 |
| $C_3$ | | 3.6 | | 1.0 |
| $iC_4$ | 0.0 | 9.2 | 0.0 | 3.2 |
| $nC_4$ | 0.0 | 4.5 | 0.0 | 1.0 |
| $iC_5$ | 56.1 | 34.1 | 56.1 | 39.8 |
| $nC_5$ | 1.8 | 11.5 | 1.8 | 13.3 |
| $iC_6$ | 39.4 | 31.4 | 38.2 | 34.6 |
| $nC_6$ | 1.1 | 4.6 | 1.1 | 5.1 |
| CP, MCP, CH, BZ | 1.5 | 0.0 | 2.8 | 0.8 |
| $C_7+$ | 0.0 | 0.2 | 0.0 | 0.7 |
| SUM | 100.0 | 100.0 | 100.0 | 100.0 |
| $iC_5 + iC_6$ converted (%) | — | 31.4 | — | 21.2 |
| $C_2, C_3, nC_4, nC_5, nC_6$ | 2.9 | 24.4 | 2.9 | 20.4 |
| CYCLICS | | | | |
| CP | 1.46 | 0.00 | 1.42 | 0.56 |
| MCP | 0.06 | 0.01 | 0.06 | 0.12 |
| CH | 0.03 | 0.01 | 1.29 | 0.08 |
| BZ | 0.00 | 0.00 | 0.00 | 0.00 |
| $C_7+$ Cyclics | 0.00 | 0.03 | 0.00 | 0.37 |
| TOTAL CYCLICS | 1.54 | 0.05 | 2.77 | 1.12 |
| Cyclics Converted (%) | — | 97.0 | — | 59.5 |
| C Conversion (%) | — | 100.0 | — | 60.9 |

In addition, as shown in Table 2, the $iC_5$ hydrocarbons and $iC_6$ hydrocarbons conversion and the ring opening conversions were lower when the $C_6$ cyclic hydrocarbons were present in the feed. It can additionally be observed that without the $C_6$ cyclic hydrocarbon, the sum of $C_2$ to $C_6$ normal paraffins in Product B were 24.4 wt % whereas with the $C_6$ cyclic hydrocarbon in the feed, the sum of $C_2$ to $C_6$ normal paraffins in Product C were less at 20.4 wt %. It can further be observed that the production of undesired methane was low in Product B.

Thus, as shown, the $iC_5$ and $iC_6$ hydrocarbons conversion and the normal paraffin yields can be increased in the isomerization zone by removing or reducing the $C_6$ cyclic hydrocarbons from the stream passed into the isomerization zone.

In a third experiment, shown in Table 3, a platinum-containing sulfated zirconia catalyst was loaded and operated under isomerization conditions of 3.1 MPa (449 psig), at a rate of 7.7 $h^{-1}$ LHSV, with a 2.1 inlet $H_2$/HC mole ratio, and 178.3° C. (353° F.) average catalyst bed temperature. The catalyst was operated with Feed D which was rich in $iC_5$ hydrocarbons and did not contain $C_6+$ cyclic hydrocarbons.

TABLE 3

| COMPONENTS (wt %) | FEED D | PRODUCT D |
|---|---|---|
| $H_2$ | | 5.2 |
| $C_1$ | | 0.7 |
| $C_2$ | | 2.0 |
| $C_3$ | | 3.1 |
| $iC_4$ | 0.0 | 5.2 |
| $nC_4$ | 0.0 | 2.9 |
| $iC_5$ | 96.8 | 55.8 |
| $nC_5$ | 3.2 | 18.8 |
| $iC_6$ | 0.0 | 5.6 |
| $nC_6$ | 0.0 | 0.8 |
| Cyclopentane (CP) | 0.0 | 0.0 |
| Methylcyclopentane (MCP) | 0.0 | 0.0 |
| Cyclohexane (CH) | 0.0 | 0.0 |
| Benzene (BZ) | 0.0 | 0.0 |
| $C_7+$ | 0.0 | 0.2 |
| SUM | 100.0 | 100.0 |
| $C_2, C_3, nC_4, nC_5, nC_6$ | 3.2 | 27.6 |

As can be appreciated from Table 3, the sulfated zirconia catalyst produced a significant amount of normal paraffins for a stream which can be used as a feed stream for a steam cracking unit (27.6 wt % yield).

In addition, the disproportionation reactions occur as demonstrated by the formation of $iC_4$ and $iC_6$ products via the reaction $2iC_5 \rightarrow iC_4 + iC_6$, the isomerization conversions are demonstrated by the formation of $nC_4$ and $nC_6$, and hydrocracking reactions are demonstrated by the formation of methane and ethane. The propane is formed via the disproportionation of $iC_4$ and possibly some other hydrocracking reactions.

Therefore, not only will the processes described herein increase the per-pass conversion of iso-paraffins to normal paraffins, the processes will do so without the need for chloride-containing catalysts, minimizing and eliminating further processing required for the feed stream to a steam cracker. The desirability of such processes is discussed above.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

What is claimed is:

1. A process for producing a feed for a steam cracker, the process comprising:

separating a portion of C6 cyclic hydrocarbons from a naphtha stream comprising C5+ hydrocarbons to provide a C6 cyclic hydrocarbons lean stream;

separating iC5 paraffinic hydrocarbons and iC6 paraffinic hydrocarbons from the C6 cyclic hydrocarbons lean stream; and, passing a feed stream comprising at least one stream being rich in iC5 paraffinic hydrocarbons, iC6 paraffinic hydrocarbons, or both to an isomerization zone containing non-chlorided catalyst comprising a sulfated zirconia or a tungstated zirconia to disproportionate at least some isoparaffins to form iC4, iC5 and iC6 paraffinic hydrocarbons, and isomerize iC4, iC5, and iC6 isoparaffins to normal paraffins to form an isomerization effluent;

separating the effluent from the isomerization zone into an overhead stream comprising C4− hydrocarbons and a bottoms stream comprising C5+ hydrocarbons; and, passing at least one stream from the isomerization zone to a steam cracker.

2. The process of claim 1 further comprising:
controlling an amount of $C_6$ cyclic hydrocarbons passed into the isomerization zone.

3. The process of claim 2 wherein the amount of $C_6$ cyclic hydrocarbons passed into the isomerization zone is controlled by at least one of the following:

selectively adding a stream of $C_6$ cyclic hydrocarbons to the isomerization zone; and, controlling an operating parameter of a separation zone used to separate the $C_6$ cyclic hydrocarbons from the naphtha stream.

4. The process of claim 1 further comprising:
passing the naphtha stream to a first separation zone; and,
separating the naphtha stream in the first separation zone into an overhead stream and a bottoms stream, the overhead stream being the $C_6$ cyclic hydrocarbons lean stream and the bottoms stream being rich in n-hexane and $C_6$ cyclic hydrocarbons.

5. The process of claim 4 further comprising:
passing the overhead stream from the first separation zone to a second separation zone; and,
separating the overhead stream from the first separation zone in the second separation zone into the at least one stream being rich in $iC_5$ isoparaffinic hydrocarbons, $iC_6$ isoparaffinic hydrocarbons, or both.

6. The process of claim 5 further comprising:
separating the overhead stream from the first separation zone in a first separator column of the second separation zone into an overhead stream, an intermediate stream, a bottoms stream,
the overhead stream from the first separator column of the second separation zone being rich in $C_5$ hydrocarbons, and,
the intermediate stream of the first separator column of the second separation zone being rich in $iC_6$ isoparaffinic hydrocarbons.

7. The process of claim 6, further comprising:
separating the overhead stream from the first separator column of the second separation zone in a second separator column of the second separation zone into an overhead stream and a bottoms stream,
the overhead stream of the second separator column of the second separation zone being rich in $iC_5$ isoparaffinic hydrocarbons.

8. The process of claim 7 further comprising:
recycling the bottoms stream from the isomerization zone to the first column from the second separation zone.

9. The process of claim 7 further comprising:
combining the bottoms stream from the first separator column and the second separator column; and,
passing the combined bottoms streams from the first separator columns and the second separator column to the steam cracker.

10. The process of claim 4 wherein the second separation zone comprises:
at least one adsorption zone.

11. The process of claim 10 further comprising:
separating the overheads stream from the first separation zone in the at least one absorption zone into a first stream and a second stream,
the first stream being rich in $iC_5$ hydrocarbons and $iC_6$ hydrocarbons and,
the second stream being rich in n-pentane and n-hexane.

12. The process of claim 11 further comprising:
recycling the bottoms stream from the isomerization zone to the first separation zone.

* * * * *